United States Patent [19]

Bartorelli et al.

[11] 4,383,985

[45] May 17, 1983

[54] BREAST CANCER ANTIGENS

[75] Inventors: Alberto Bartorelli, Milan; Roberto Accinni, Barlassina, both of Italy

[73] Assignee: Hoffmann-La Roche Inc., Nutley, N.J.

[21] Appl. No.: 167,567

[22] Filed: Jul. 11, 1980

Related U.S. Application Data

[63] Continuation of Ser. No. 867,076, Jan. 5, 1978, abandoned.

[30] Foreign Application Priority Data

Jan. 12, 1977 [GB] United Kingdom ............... 1140/77

[51] Int. Cl.³ ............... G01N 33/58; G01N 33/60; C07G 7/00; A61K 43/00
[52] U.S. Cl. ............... 424/1; 260/112 R; 260/112 B; 424/85; 424/88; 436/543; 436/545; 436/542
[58] Field of Search ............... 260/112 R, 112 B; 424/1, 12, 85, 88; 23/230 B

[56] References Cited

U.S. PATENT DOCUMENTS

| | | | |
|---|---|---|---|
| 3,410,839 | 11/1968 | De Carvallto | 260/112 B |
| 3,823,126 | 7/1974 | Bjorklund | 260/112 R |
| 3,956,258 | 5/1976 | Hansen | 260/112 R |
| 3,960,827 | 6/1976 | Bjorklund | 260/112 R |
| 4,132,769 | 1/1979 | Osther | 260/112 R X |

OTHER PUBLICATIONS

Chem. Abstracts, vol. 74, 1971, 21345j, Taylor et al.
Chem. Abstracts, vol. 86, 1977, 104321a, Bartorelli et al.
Clinical Chemistry, 22/6, 733-738; 1243-1255, (1976), Scharpe et al.
Nature; 203, Sep. 1964, pp. 1186-1188, De Carvallto.

*Primary Examiner*—Christine M. Nucker
*Attorney, Agent, or Firm*—Jon S. Saxe; George M. Gould; Peter R. Shearer

[57] ABSTRACT

Tumor associated antigens are disclosed in both crude and pure form which are specific to human breast cancer. The antigens are designated BCA. Antisera, radiolabeled antigens and antisera, as well as methods for the detection of circulating BCA are also disclosed. Methods for the extraction of BCA also form part of the invention. A diagnostic kit for the detection of circulating BCA, especially one suitable for use in as radioimmunoassay is also disclosed.

21 Claims, No Drawings

BREAST CANCER ANTIGENS

This is a continuation of application Ser. No. 867,076 filed Jan. 5, 1978 now abandoned.

BACKGROUND OF THE INVENTION

In 1965 a tumor associated antigen was found (*J. Exptl. Med.* 121 439-462, 1965) which was subsequently designated as carcinoembryonic antigen (hereinafter CEA). CEA circulates and may be detected in human blood—serum or plasma—by a radioimmunoassay. However it does not appear to be associated with breast cancer.

We have now suceeded in locating, isolating and purifying a series of antigens which are associated with breast cancer tumors. These were initially designated "MK" and "fractionated MK" but we have now designated them BCA-Breast Cancer Antigens. "MK" and "fractionated MK" may be regarded as crude and pure forms of BCA respectively.

SUMMARY OF INVENTION

This invention thus relates to novel antigens associated with breast carcinoma (designated BCA) and extractable in a manner substantially as herein described, anti-sera specific to said antigens, radiolabeled forms of said antigens and methods of detecting said antigens circulating in serum or plasma. The invention also relates to a diagnostic kit containing standard antigens or antisera or marked forms thereof for the detection of said antigens in human blood.

DETAILED DESCRIPTION OF INVENTION

The isolation and purification of breast cancer antigens-BCA may be carried out by any convenient method. Such methods normally involve homogenisation of the relevant tissue, extraction with a glycoprotein solvent and finally chromatography on one or more columns. Initially crude BCA may be isolated and purified on the basis of its property of crossreacting with CEA-antiserum, but once crude BCA-antiserum has been made available following on from the first isolation, the isolation and purification can be effected using crude BCA-antiserum as a guide during subsequent extraction and isolation procedures.

Pure BCA requires more complicated isolation methods since it does not cross-react with CEA-antiserum.

Of the methods available for the isolation and purification of crude BCA and pure BCA, the ones most conveniently used are solvent extraction, ion-exchange (absorption) chromatography, or gel filtration or a combination thereof. Usually a combination of all three methods is employed.

The solvents which may be employed are glycoprotein solvents. The preferred solvent is aqueous ammonium sulfate, preferably about 80% saturated. Other solvents which may be used include potassium chloride and perchloric acid.

Gel filtration is normally effected using a hydrophilic water-insoluble cross-linked dextran polymer gel. This gel material is commercially available from AB Pharmacia, Uppsala, Sweden under the name "Sephadex" and comprises a three dimensional macroscopic network of dextran substances bonded or cross-linked together, being capable of absorbing water with swelling. In the extraction described hereinafter "Sephadex G-200" was employed, the "200" indicating a water regain value of about 20 ml/g dry gel.

For ion-exchange chromatography, diethylaminoethyl cellulose (hereinafter DEAE) is preferred for the isolation of crude BCA and pure BCA. The diethylaminoethyl celluloses which are most suitable are those which are microgranular in form, have rod shaped particles with a particle size distribution, expressed as diameter of equivalent spheres, within a range of about $20\mu$ to about $60\mu$, have a capacity of $1.0\pm0.1$ meq/gm. a water regain of 2.3–2.9 gm/gm dry exchanger and are in free base form.

The elution medium used may be any medium which can be formulated so as to separate the desired antigens. It has been found that sodium phosphate buffers having a pH of from about 7.0 to 7.5 may be employed for this purpose. Elution may be carried out using serial dilutions of the buffer or a gradient.

When using two consecutive chromatography steps eg. absorption and gel-filtration, they may be employed in either order.

Although crude BCA cross-reacts with CEA indicating that the two antigens have some antigenic sites in common, sufficient immunological, and physico-chemical differences are apparent to enable one to say that the two antigens are distinct from one another. Pure BCA is clearly quite distinct from CEA since it does not cross-react with CEA-antiserum. Immunological tests have also been carried out to demonstrate that crude BCA and pure BCA are distinct from CCA III (Colon carcinoma antigen III—see Federal Proceedings Faseb 31 No. 2, 1972, Abstract No. 2398) which according to its physical chemistry and its immunochemistry is probably identical to NGP (Normal glycoprotein—see Immunochemistry 9, 1972 pages 1031–1034) and also distinct from NCA (non-specific cross-reacting antigen—see Proc. Nat. Acad. Sci 69, 1972, pages 2492–2494).

The BCA antigens may be detected by conventional methods in breast cancer patients and since the antigens circulate, them may be detected at a very early stage of neoplastic growth. Detection is thus of great value in the early diagnosis of breast cancer. The most preferred method of detecting circulating antigens is by means of a radioimmunoassay. Another preferred technique is that of enzyme labelling. This latter technique is described in the reviews in Clinical Chemistry volume 22 at pages 733 to 738 and 1243 to 1255. Other methods may however also be used such as for example haemaglutination assay, immunodiffusion, countercurrent electrophoresis, complement fixation technique and latex agglutination.

Antisera for both crude BCA and pure BCA may be prepared in a conventional manner e.g. using rabbits. BCA and also antisera specific to BCA may likewise be radiolabeled in a conventional manner e.g. using the modified method of Hunter and Greenwood.

The method according to the invention for detecting BCA circulating in blood-serum or plasma comprises carrying out the following steps:

(a) adding a specific amount of BCA-antiserum to an blood sample,
(b) incubating the mixture,
(c) adding a specific amount of radioactive labeled BCA
(d) incubating the mixture,
(e) separating the BCA-anti BCA complexes from free BCA, (f) measuring the radioactivity of either the complexes or the free BCA.

The invention also comprises an diagnostic kit for the detection of BCA in a sample, which contains BCA and/or BCA-antiserum. The BCA and/or BCA-antiserum may be labeled with a radioactive isotope which may conveniently be $I^{125}$.

The invention will now be illustrated with reference to the following Examples.

The radioimmunoassay used in Examples 2-5 to check the progress of the chromatography steps used was carried out as follows:

The double antibody technique was employed: serial amounts of the crude extracts (from 100 to 3.12 μg) were incubated for 24 hr at 37° C. with $^{125}I$ CEA and 1:200,000 absorbed anti-CEA. For the bound/free separatiton, 1:100 antigoat gamma globulin rabbit serum and 1:5,000 normal rabbit serum were added. After a second incubation, 1 hour at 37° C., and 20 min. at 4° C. the samples were centrifuged at 5,000×g for 15 min. and the supernatant was discarded by suction. The precipitate was counted for 1 minute in an auto-gamma-counter Packard 5130 (70% efficiency).

EXAMPLE 1

A pool of histologically different human primary breast carcinomas was collected. No metastatic tissue was used. The tissues were homogenized, extracted with 3 M KCl in $5 \times 10^{-3}$ M sodium phosphate buffer at pH 7.4 and then centrifuged (45,000×g for 1 hour). The supernates were dialyzed exhaustively against distilled water and then lyophilized. The crude extract resulting from the foregoing procedure was resuspended in sodium phosphate buffer at pH 7.2 (0.04 M sodium phosphate+0.1 M NaCl) at a concentration of 30 mg/ml. 1.5 ml of the solution was purified by gel-filtration on a 1.5×70 cm Sephadex G-200 column and eluted with sodium-phosphate buffer pH 7.2 (flow rate: 4 ml/cm²/hour). Crude BCA was obtained in those fractions (14-16) which showed the highest cross-reaction with CEA in a competitive inhibition with $^{125}I$-CEA-anti-CEA.

EXAMPLE 2

A pool of human primary breast carcinomas was homogenized in an ice bath, lyophilized, extracted at 4° C. with 3 M KCl in a phosphate buffer (0.005 M Na₂HPO₄—NaH₂PO₄—pH 7.5), 1:100 w/v ratio and centrifuged at 100,000×g for 1 hour. The supernatant was dialyzed, first against tap water, and then against distilled water, until all the chloride had been removed, and concentrated by ultrafiltration (P.S.A.C. Millipore Corporation, Bedford, Mass.) and lyophilized. 800 mg of the lyophilized extract was resuspended in 40 ml of a phosphate buffered saline (0.05 M NaH₂PO₄—Na₂HPO₄—pH 7.2 containing 0.1 M NaCl) (hereinafter PBS buffer) and centrifuged at 100,000×g for 1 hour, giving a crude extract of primary breast cancer—crude BCA. The protein concentration of the supernatant determined by the Lowry technique (using albumin as the standard) was 11.2 mg/ml. 7.5 ml (20 mg/ml) of the crude BCA was gel filtered on a Sephadex G 200 column (2.5×110 cm) eluted with the PBS buffer at a flow rate of 4 ml/cm²/hr. The eluates were read at 280 nm and 50 μl of every fraction (5 ml) were checked by a radioimmunoassay against $^{125}I$ CEA anti-CEA. Fractions 52-65 and 66-78, obtained from the gel filtration were combined, dialyzed, concentrated by ultrafiltration and lyophilized. The yields were as follows: Fractions 52-65=71.55 mg; Fractions 66-78=55.68 mg. The lyophilized product was resuspended in phosphate buffered saline—PBS—(20 mg/ml) and then centrifuged for 1 hr at 100,000×g. The supernatant (3 ml), checked by Lowry's method (14 mg/ml), was gel filtered on a Sephadex G 200 column (1.5×105 cm) (flow rate: 4 ml/cm²/hr). The eluates were read at 280 nm and a 200 μl aliquot of every fraction (4 ml) was checked by a radioimmunoassay against a $^{125}I$ CEA anti-CEA system as described above. Fractions 18-30, obtained from gel filtration were dialyzed against a phosphate buffer and chromatographed on a diethylaminoethyl cellulose column (1.5×20 cm) (23 S. S. Serva) equilibrated with phosphate buffer. The diethylaminoethyl cellulose column was eluted at a flow rate of 20 ml/cm²/hr with phosphate buffers of varying molarity (0.005 M; 0.025 M; 0.05 M; 0.1 M; 0.5 M). The fractions (10 ml each) contained in the peak (read at 280 nm) were pooled, dialyzed and concentrated by means of ultrafiltration up to 3.5 ml of crude BCA and checked by a radioimmunoassay against $^{125}I$ CEA-anti-CEA.

EXAMPLE 3

60 g of a lyophilized homogenate of a pool of human primary breast carcinomas was dissolved in 450 ml of double distilled water and 450 ml of cold 2 N perchloric acid were then added dropwise with stirring. The perchloric acid extract was centrifuged at 4,500×g for 30 min. The lyophilized homogenate was extracted once again with 1 N perchloric acid. After pooling the supernatants were dialyzed against tap water for 12 hr, and then against double distilled water for 36 hr. The solutions were concentrated by ultrafiltration and lyophilized. The lyophilized lots were dissolved in 3 M potassium chloride in phosphate buffer and stirred at 4° C. for 24 hr. After centrifugation at 100,000×g for 1 hr the supernatant was dialyzed, concentrated by ultrafiltration and lyophilized. The yield was 1.4% 500 mg of this lyophilized material was suspended in 25 ml of phosphate buffered saline—PBS—and centrifuged at 100,000×g for 1 hr. The supernatant was checked using Lowry's method (13.4 mg/ml) and by the radioimmunoassay against $^{125}I$ CEA anti-CEA. 10 ml (20 mg/ml) of the supernatant was chromatographed on a diethylaminoethyl cellulose column (2.8 cm×15 cm) as described in Example 2. Fractions (5 ml each) were checked at 280 nm. 200 μl of each fraction was tested by a radioimmunoassay against $^{125}I$ CEA anti-CEA as described above.

The fractions, for each molarity step of the eluant, according to the U.V. absorption and the response to the radioimmunoassay, were pooled, concentrated by ultrafiltration and then lyophilized. 20 mg of the lyophilized material resulting from elution with the 0.05 M buffer were dissolved in 2 ml of phosphate buffered saline—PBS. After centrifugation at 100,000×g for 1 hr the supernatant containing the crude BCA was checked by Lowry's method and found to contain 7 mg/ml. 0.5 ml of the supernatant was then gel filtered on a Sephadex G 200 column (1×95 cm); and eluted with phosphate buffered saline—PBS—at a flow rate of 6 ml/cm²/hr. Each fraction (1.4 ml) from the gel filtration was checked for absorption at 280 nm and also by a radioimmunoassay against $^{125}I$ CEA anti-CEA as described above. Fractions 21-27 from the gel filtration were pooled, dialyzed and concentrated by ultrafiltration to 1 ml. After centrifugation at 100,000×g for 1 hr, 10 ml aliquots of the supernatant containing crude BCA were labeled, gel filtered on Sephadex G 200 and checked by the above described radioimmunoassay against anti-crude BCA.

EXAMPLE 4

A crude BCA extract prepared as described above in Example 1 was chromatographed on a diethylaminoethyl cellulose column as follows. 200 mg of crude extract were dissolved in 40 ml of 0.005 M sodium-phosphate buffer, pH 7.5. The solution was applied to a 2.4×30 cm diethylaminoethyl cellulose (23 S. S. Serva) chromatography column that had been equilibrated with the 0.005 M phosphate buffer, pH 7.5. The column was eluted stepwise with a series of phosphate buffers at pH 7.5 (0.005 M, 0.025 M, 0.1 M and 0.5 M). 10 ml fractions were collected at a flow rate of 20 ml/hour. The absorbancy of each fraction was read at 280 nm, thereby defining the peaks. The fifth peak was the one that showed by far the highest immunological activity with anti-CEA. The fractions comprising this peak were combined and dialyzed against sodium-phosphate buffer (0.04 M sodium-phosphate+0.1 M NaCl) at pH 7.2. The protein concentration was adjusted to 750 $\mu$g/ml. The material was then concentrated and purified by gel filtration on a 1.5×70 cm Sephadex G-200 column. A 1.5 ml portion of the concentrate was applied to the column and eluted with sodium-phosphate buffer at pH 7.2; 4 ml fractions were collected at a flow rate of 4 ml/cm$^2$/hr. Fraction No. 18, which showed the highest activity with anti-CEA, was concentrated to 1 mg/ml and 10 $\mu$l were labeled with Na$^{125}$I according to the modified method of Hunter and Greenwood. This labeled material was again chromatographed by gel filtration on a 1×100 cm Sephadex G-200 column with sodium-phosphate buffer at pH 7.2. Fractions of 1.5 ml were collected at a flow rate of 8 ml/cm$^2$/hour. Fraction No. 18 was again collected. This fraction reacted with an anti-serum prepared from crude BCA but not with anti-CEA. This fraction thus contains antigens (BCA) associated with breast carcinoma that do not crossreact with anti-CEA and react only with an antibody produced using antigens extracted from this type of tumor.

EXAMPLE 5

To 15 ml of crude BCA prepared as described in Example 2 (10 mg/ml) in a phosphate buffer 8.4 g of (NH$_4$)$_2$SO$_4$ equivalent to 80% saturation were slowly added. After stirring for 20 min., the product was centrifuged at 15,000×g for 15 min. The precipitate was then resuspended in 8 ml of phosphate buffer—PBS—. The resuspended precipitate (crude BCA) and the supernatant, after dialysis against phosphate buffered silane. PBS buffer, were checked by the radioimmunoassay against $^{125}$I CEA anti-CEA. The protein content was 10 mg/ml according to Lowry's method. The resuspended crude BCA was then chromatographed on a diethylaminoethyl cellulose column as described above in Example 2. The fractions from the elution using 0.05 M phosphate buffer—PBS—which were active according to a radioimmunoassay against $^{125}$I CEA-anti-CEA were pooled (16 ml) concentrated by ultrafiltration (P.S.A.C.) to 3 ml, and then centrifuged at 100,000×g for 1 hr. The supernatant was gel filtered on a Sephadex G 200 column (1.05×105 cm) at a flow rate of 10 ml/cm$^2$ hr. The elution fractions were checked by the above described radioimmunoassay against $^{125}$I CEA anti-CEA and $^{125}$I CEA anti-crude BCA (from Example 3). The most active fractions against $^{125}$I CEA anti-crude BCA were pooled (10 ml) (Lowry: 80 $\mu$g/ml) and concentrated to 1.8 ml. After centrifugation at 100,000×g for 1 hr, the protein content of the supernatant (Breast Cancer Antigen(s): BCA) was determined by Lowry's method (350 $\mu$g/ml).

EXAMPLE 6

10 $\mu$l of a solution of BCA having a concentration of 1 mg/ml was mixed with 10 $\mu$l of $^{125}$I Na (=1 mci) in the presence of Chloramine T (50 ml of a solution containing 16 mg/10 ml). The mixture was allowed to react for 55 seconds at the ambient temperature. 50 $\mu$l of solution of sodium metabisulfite were then added (concentration 48 mg/10 ml). The reaction product was then separated from free iodine-125 by chromatography on a Sephadex G-200 column eluted at the rate of 8 ml/cm$^2$/hr.

A radioimmunoassay was carried out using plasma (5 ml of blood taken up in 0.1 ml of EDTA solution). The first incubation was carried out at 37° C. for 24 hours using 0.1 ml of the plasma sample and rabbit anti-BCA (which had been absorbed with normal tissue extract). The radiolabeled antigen marked as described above was then added. The antigen had an activity of 20,000 CPM/0.1 ml. The mixture was then incubated a second time for 24 hours at 37° C. A third incubation was then carried out with anti-gammaglobulin diluted fourfold from the rabbit used to prepare the antiserum. Centrifugation was then carried out at 6000×g for 15 minutes and the precipitate was then counted in a $\gamma$-counter after the supernates had been aspirated off.

What is claimed is:

1. Breast cancer antigens, designated "BCA", and characterized as follows:
    (a) being endogenous to and extractable with a glycoprotein solvent from human primary breast carcinomas,
    (b) unreactive with carcinoembryonic antigen antiserum,
    (c) reactive only with antiserum produced by antigens extracted from human primary breast carcinomas, and
    (d) essentially free of other endogenous material.
2. BCA-antiserum specific to BCA, said BCA being as claimed in claim 1.
3. Radiolabeled BCA, said BCA being as claimed in claim 1.
4. Radiolabeled BCA-antiserum, said BCA being as claimed in claim 1.
5. Radiolabeled BCA labeled with I$^{125}$, said BCA being as claimed in claim 3.
6. Enzyme labeled BCA, said BCA being as claimed in claim 1.
7. An immunoassay method for detecting breast cancer antigens, designated BCA, said BCA being as claimed in claim 1 and circulating in a serum or plasma sample, which method comprises:
    (a) adding a specific amount of BCA-antiserum to the sample,
    (b) incubating the resulting mixture of step (a),
    (c) adding a specific amount of labeled BCA to the mixture,
    (d) incubating the mixture,
    (e) separating the resulting BCA-anti BCA complexes from free BCA,
    and (f) measuring the activity of the labeled BCA of either the complexes or the free BCA, in order to detect the BCA of the sample.

8. A method as claimed in claim 7 wherein the labeled BCA is radioactively labeled BCA.

9. A method as claimed in claim 7 wherein labeled BCA is fluorescent labeled BCA.

10. A diagnostic test kit for the detection of breast cancer antigens, designated BCA, in a serum or plasma sample, said BCA being as claimed in claim 1, the kit comprising in combination:
(a) a container containing a specific amount of BCA-antiserum, and
(b) another container containing a specific amount of radiolabeled BCA, said BCA-antiserum and radiolabeled BCA being capable of providing radiolabeled immunocomplexes containing the BCA of the sample when the sample is treated with said BCA-antiserum and radiolabeled BCA.

11. A diagnostic kit as claimed in claim 10 wherein the radiolabel is $I^{125}$.

12. A diagnostic test kit for the detection of breast cancer antigens (BCA) in a serum or plasma sample, said BCA being as claimed in claim 1, the kit comprising in combination:
(a) a container containing a specific amount of BCA, and
(b) another container containing a specific amount of radiolabeled BCA-antiserum,
said BCA and radiolabeled BCA-antiserum being capable of providing radiolabeled immunocomplexes containing the BCA of the sample when sample is treated with said BCA and radiolabeled BCA-antiserum.

13. A diagnostic kit as claimed in claim 12 wherein the radiolabel is $I^{125}$.

14. Breast cancer antigens extracted from human primary breast carcinoma by a process comprising:
(a) extracting homogenized human primary breast carcinoma material with a glycoprotein solvent;
(b) centrifuging said extract;
(c) dialyzing the resultant supernate;
(d) lyophilizing the resultant dialysate;
(e) resuspending the resultant lyophilized dialysate in a buffered saline solution;
(f) subjecting the resulting suspension to gel filtration; and isolating the fractions containing said breast cancer antigens.

15. Breast cancer antigens of enhanced purity obtained by a process which comprises:
(a) subjecting the isolated fractions containing breast cancer antigen obtained in step (f) of claim 14 to chromatography on a diethylaminoethyl cellulose column (DEAE) and collecting from the DEAE the fractions containing said breast cancer antigens;
(b) dialyzing the DEAE collected fractions;
(c) subjecting the resulting dialysate to gel filtration; and
(d) isolating the fraction of the gel filtration containing said breast cancer antigens.

16. Breast cancer antigens according to claims 14 or 15, which antigens are radiolabeled.

17. Breast cancer antigens according to claim 16, wherein the radiolabel is $^{125}I$-iodine.

18. Breast cancer antigens according to claims 14 or 15, which antigens are enzyme labeled.

19. Breast cancer antigen according to claim 14, wherein in step (a) extraction is performed on a lyophilized homogenized human primary breast carcinoma.

20. A process for the extraction of breast cancer antigen (BCA) from human primary breast carcinoma, the process comprising:
(a) extracting homogenized human primary breast carcinoma material with a glycoprotein solvent;
(b) centrifuging the resulting extract;
(c) dialyzing the resulting supernate;
(d) lyophilizing the resulting dialysate;
(e) resuspending in a buffered saline solution;
(f) submitting the suspension to gel filtration; and isolating the resulting fractions containing BCA.

21. A process according to claim 20 further comprising:
(a) subjecting the BCA obtained in step (f) of claim 20 to chromatography on a diethylaminoethyl cellulose column and collecting the fractions containing said breast cancer antigens;
(b) dialyzing the collected fractions; and
(c) collecting the resultant dialysate.

* * * * *